US00PP30848P3

(12) United States Plant Patent
Cerny et al.

(10) Patent No.: US PP30,848 P3
(45) Date of Patent: Aug. 27, 2019

(54) APPLE TREE NAMED 'UEB 6581'

(50) Latin Name: ***Malus domestica* (Borkh.)**
Varietal Denomination: UEB 6581

(71) Applicant: Institute of Experimental Botany AS CR, v.v.i. (UEB), Prague (CZ)

(72) Inventors: Radek Cerny, Ricany u Prahy (CZ); Jan Zima, Turnov (CZ); Otto Louda, Pencin u Liberce (CZ); Jaroslav Tupy, Prague (CZ)

(73) Assignee: Institute of Experimental Botany AS CR, v.v.i. (UEB), Prague (CZ)

( * ) Notice: Subject to any disclaimer, the term of this patent is extended or adjusted under 35 U.S.C. 154(b) by 0 days.

(21) Appl. No.: 15/932,497

(22) Filed: Mar. 7, 2018

(65) Prior Publication Data

US 2018/0263154 P1 Sep. 13, 2018

Related U.S. Application Data

(60) Provisional application No. 62/600,978, filed on Mar. 8, 2017.

(51) Int. Cl.
*A01H 5/00* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

(56) References Cited

PUBLICATIONS

UPOV: PLUTO—Plant Variety Database; Feb. 9, 2019, cultivar 'UEB6581' (1page).*

* cited by examiner

*Primary Examiner* — Susan McCormick Ewoldt
(74) *Attorney, Agent, or Firm* — The Webb Law Firm

(57) ABSTRACT

A new and distinct *Malus domestica* (Borkh.) late ripening, dessert variety that exhibits weak vigor, extensive branching, $V_f$-resistance against scab, and medium-sized, dark red fruits with rare russeting. The fruits of the new variety are very sweet with very low acidity and taste similar to tropical fruits.

10 Drawing Sheets

Botanical classification: *Malus domestica* (Borkh.).
Varietal denomination: 'UEB 6581'.

BACKGROUND OF THE INVENTION

The present invention comprises a new and distinct cultivar of apple tree botanically classified as *Malus domestica* (Borkh.) and known by the varietal name 'UEB 6581'.

The new variety is the result of a cross in a planned breeding program between 'Fuji' (female parent, unpatented) and 'UEB 3264/2' (male parent, U.S. Plant Pat. No. 15,963). The cross resulting in 'UEB 6581' occurred in the Spring of 2000 at 310 meters above sea level with a mean annual temperature of 7.7° C. and a mean annual precipitation of 680 mm. The purpose of the breeding program was to develop a late ripening apple variety having red colored fruits with a sweet taste that exhibits $V_f$-resistance against scab. The new variety was discovered in 2009 with the first flowering and fruiting of the original seedling in the Czech Republic. Subsequently, the new variety was asexually reproduced in Pencin u Liberce in the Czech Republic by budding/grafting on apple rootstocks in the Spring of 2010.

The new variety is similar to its female parent, 'Fuji', in exhibiting thin one year old shoots, a large area of fruit overcolor, and a late time of eating maturity. However, 'UEB 6581' exhibits a conical fruit shape, late harvesting time, and $V_f$-resistance against scab, while 'Fuji' exhibits a globose fruit shape, very late harvesting time, and lacks $V_f$-resistance against scab. The new variety is similar to its male parent, 'UEB 3264/2', in exhibiting weak to medium tree vigor, a spreading tree growth habit, a late harvesting time, and $V_f$-resistance against scab. However, 'UEB 6581' exhibits a conical fruit shape and a relatively large area of red to dark red hue of overcolor, while 'UEB 3264/2' exhibits a globose fruit shape and relatively small area of orange hue of overcolor.

Further, when compared to apple tree named 'Red Topaz' (U.S. Plant Pat. No. 18,895), both varieties exhibit a ramified tree growth type, red fruit skin color, and $V_f$-resistance against scab. However, 'UEB 6581' exhibits conical-shaped fruits with a late time of eating maturity, while 'Red Topaz' exhibits obloid-shaped fruits with a medium to late time of eating maturity.

The following characteristics also distinguish the new variety from other varieties known to the breeders:

Late ripening, dessert, diploid variety;
Ramified tree growth type with a spreading growth habit;
Weak to medium tree vigor;
Thin one year old shoots;
Medium time to beginning of flowering;
Fruit shape is conical;
Overcolor having a red to dark red hue;
Late harvesting and time of eating maturity; and
Resistance against scab on $V_f$-gene basis.

The new variety has been trial and field tested and has been found to retain its distinctive characteristics and remain true to type through successive asexual propagations.

DESCRIPTION OF THE DRAWINGS

The accompanying photographic drawings illustrate the new cultivar taken at varying ages of maturity as recited further below, with the color being as nearly true as possible with color illustrations of this type. It should be noted that colors may vary with growing conditions and time of year.

DESCRIPTION OF THE PLANT

Figure 1:
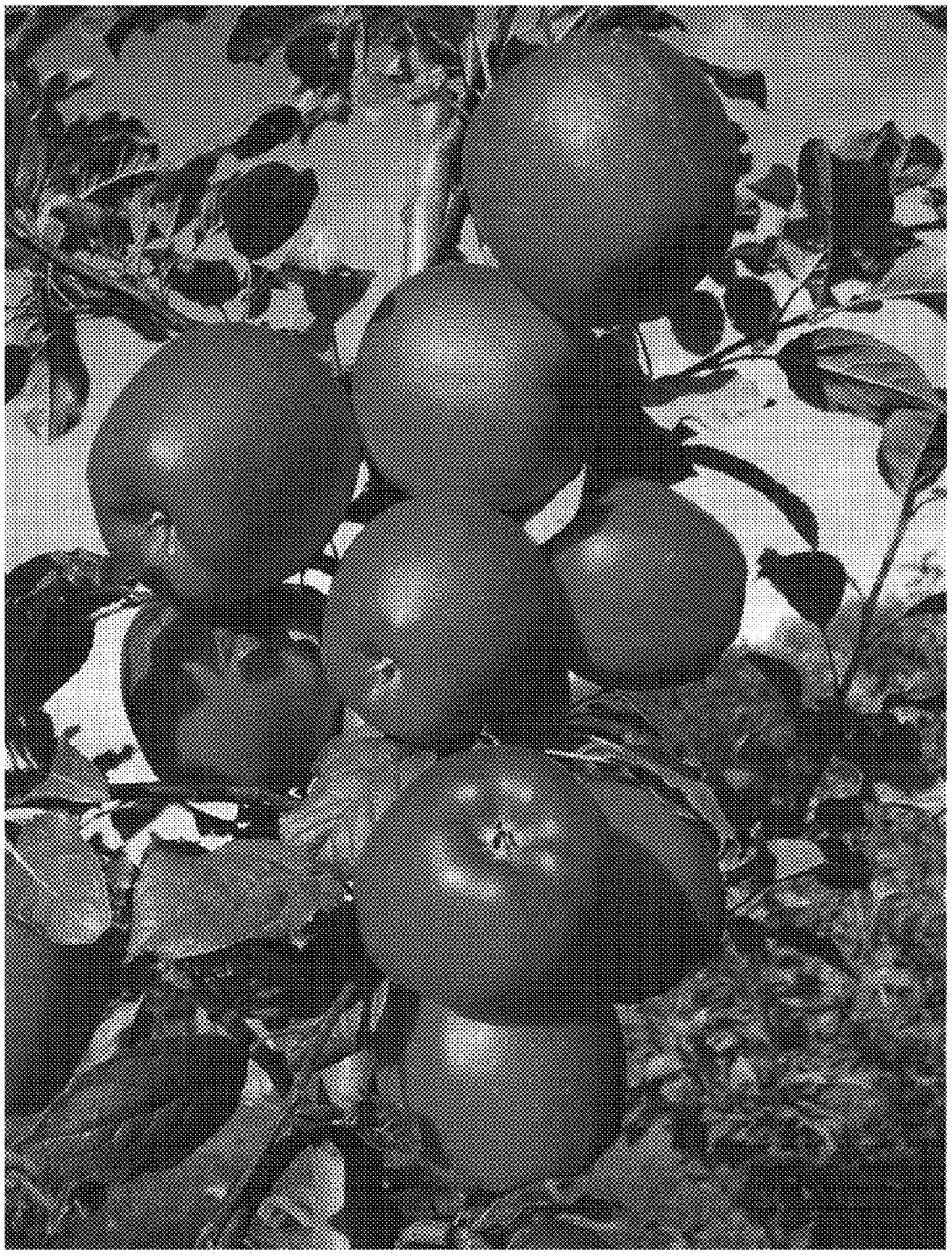
FIG. 1 illustrates details of fruits of the new variety at picking maturity from a 5-year old tree, grafted on M25 rootstock.
Figure 2:
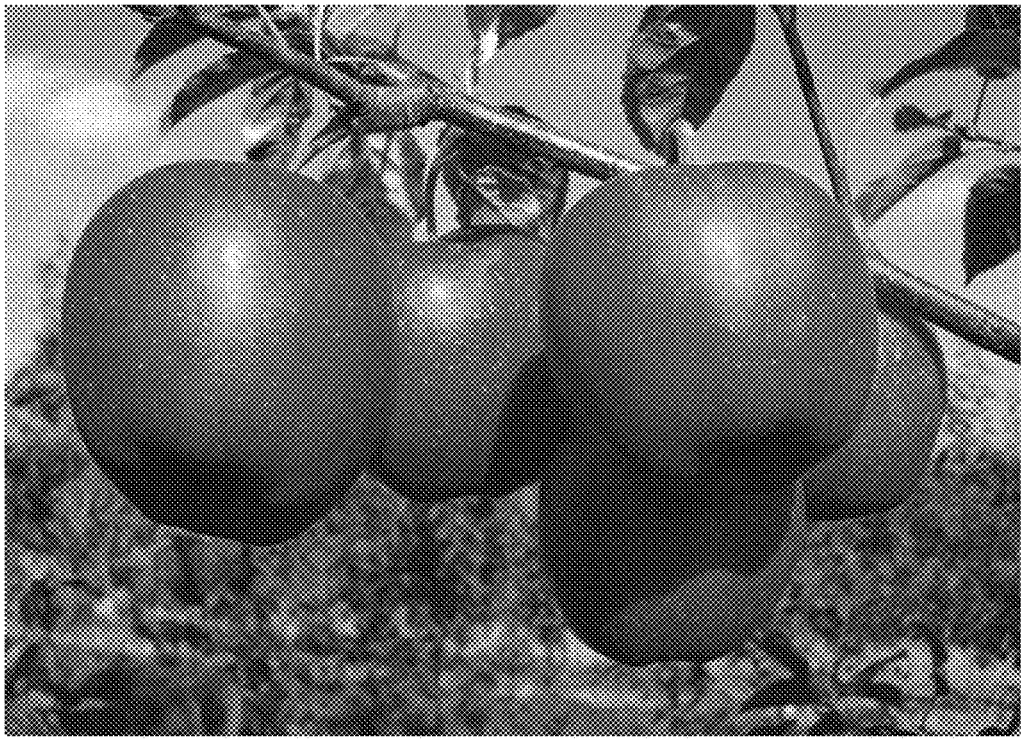
FIG. 2 illustrates details of fruits of the new variety at picking maturity from a 5-year old tree, grafted on M9 rootstock.
Figure 3:
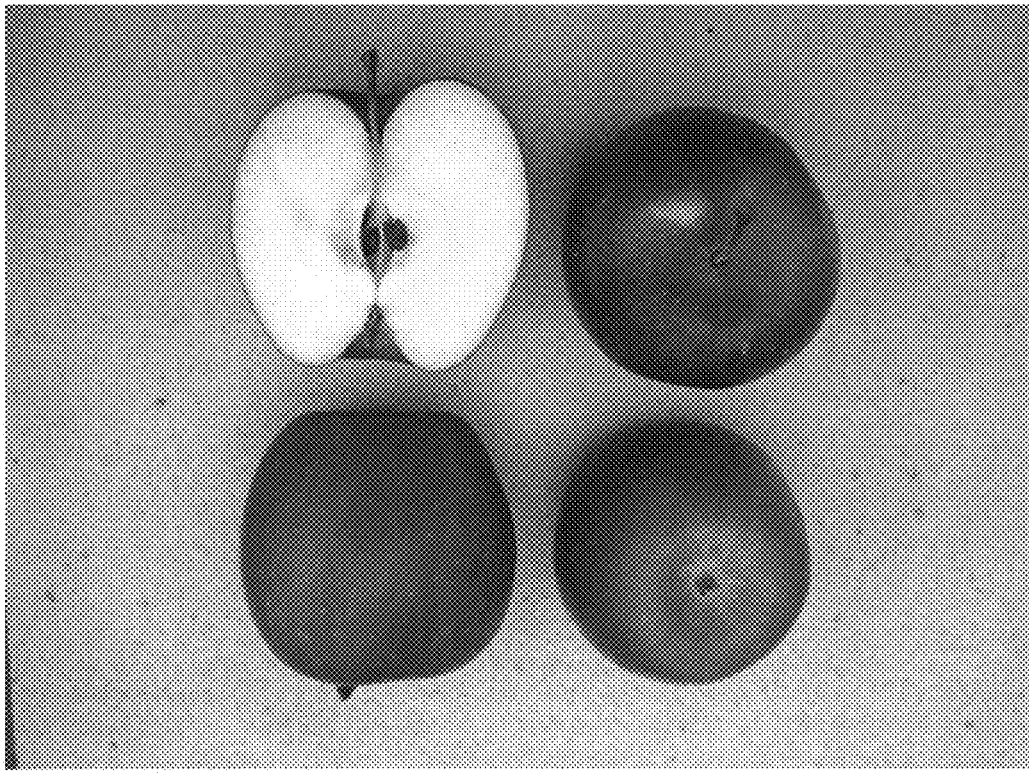
FIG. 3 illustrates details of fruits of the new variety at eating maturity from a 5-year old tree.
Figure 4:
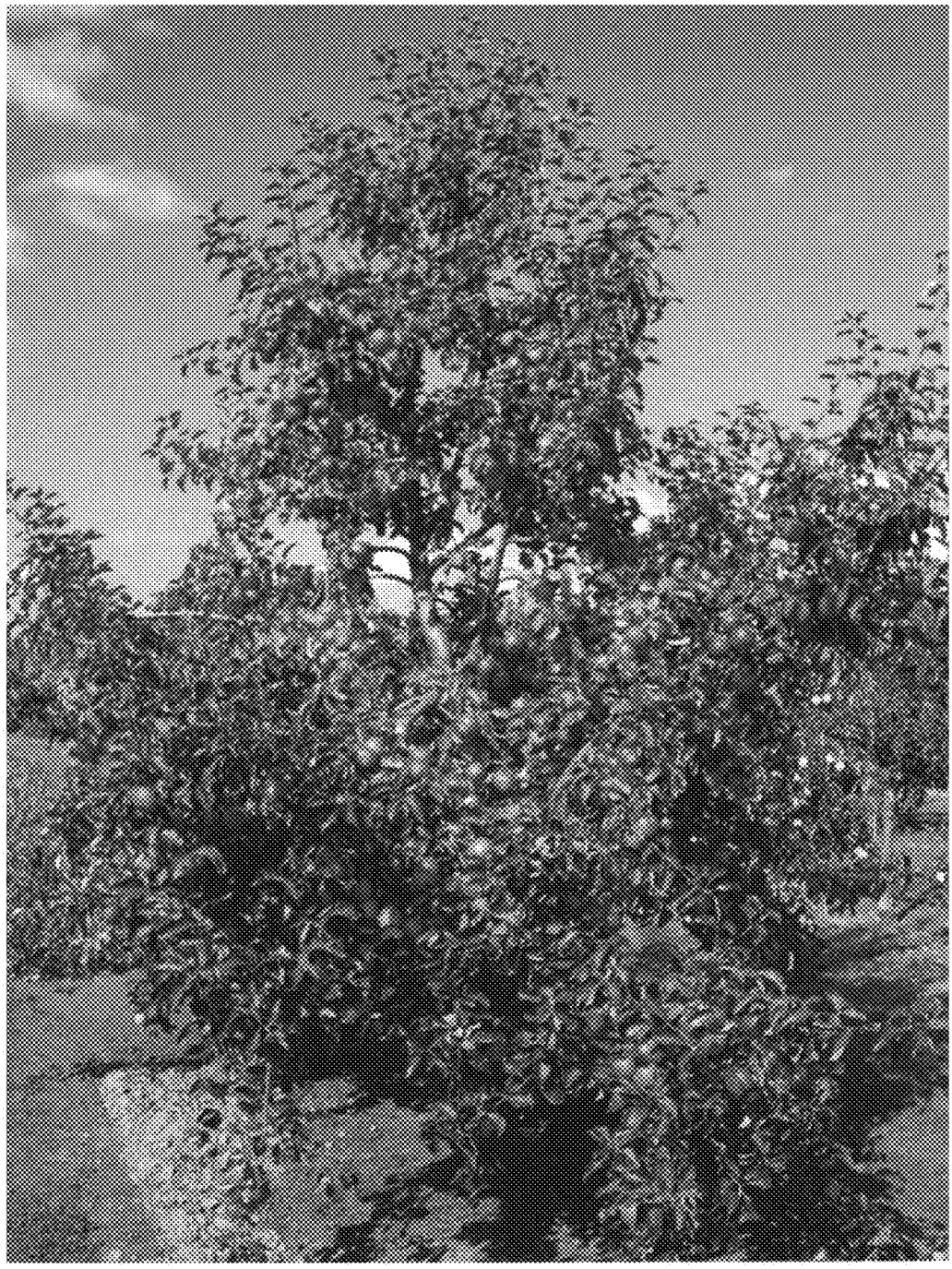
FIG. 4 illustrates the original tree of the new variety at approximately 9 years of age, showing the tree habit at picking maturity.
Figure 5:
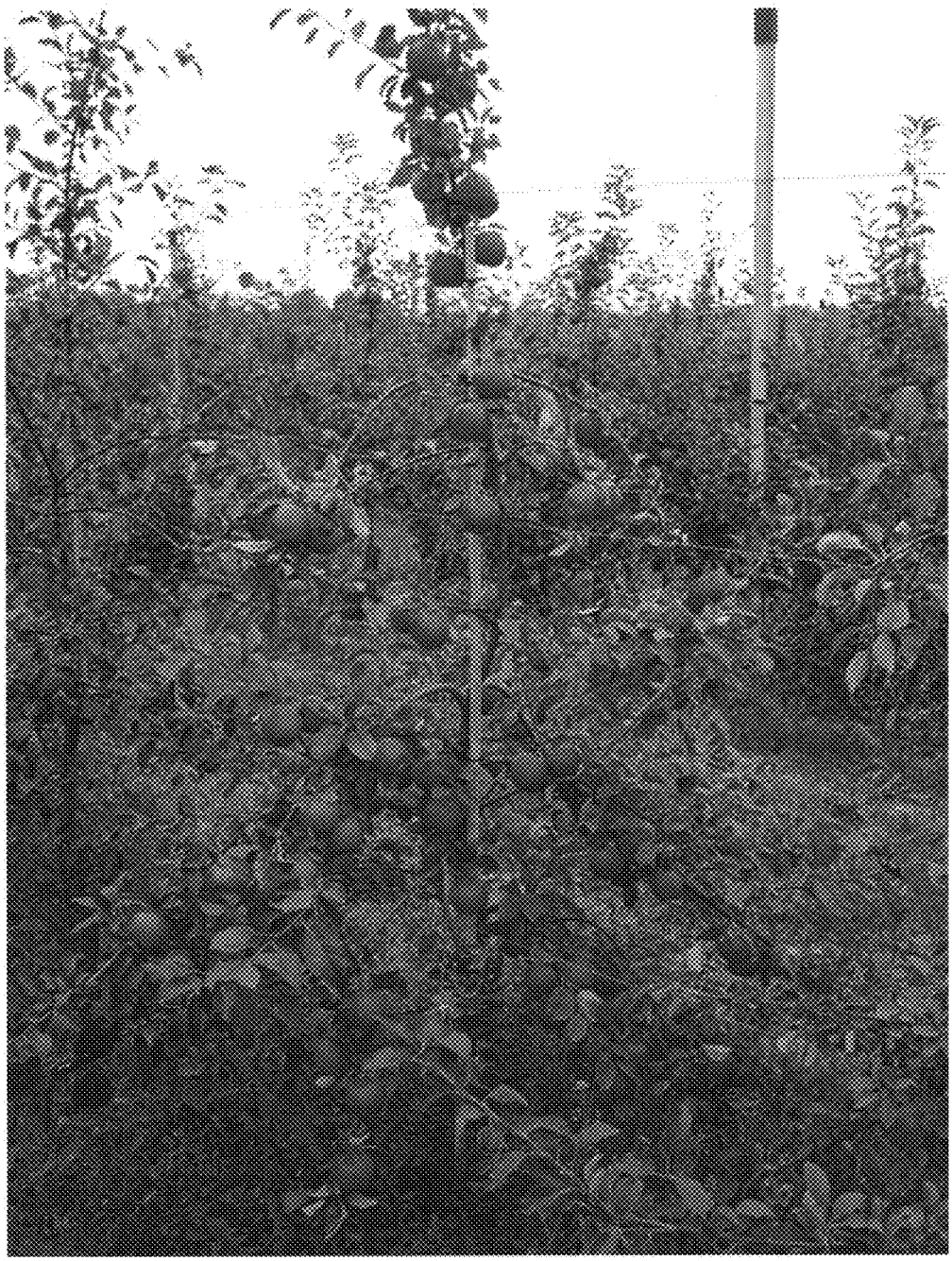
FIG. 5 illustrates a young tree of the new variety at picking maturity at 5 years of age, grafted on M9 rootstock.
Figure 6:
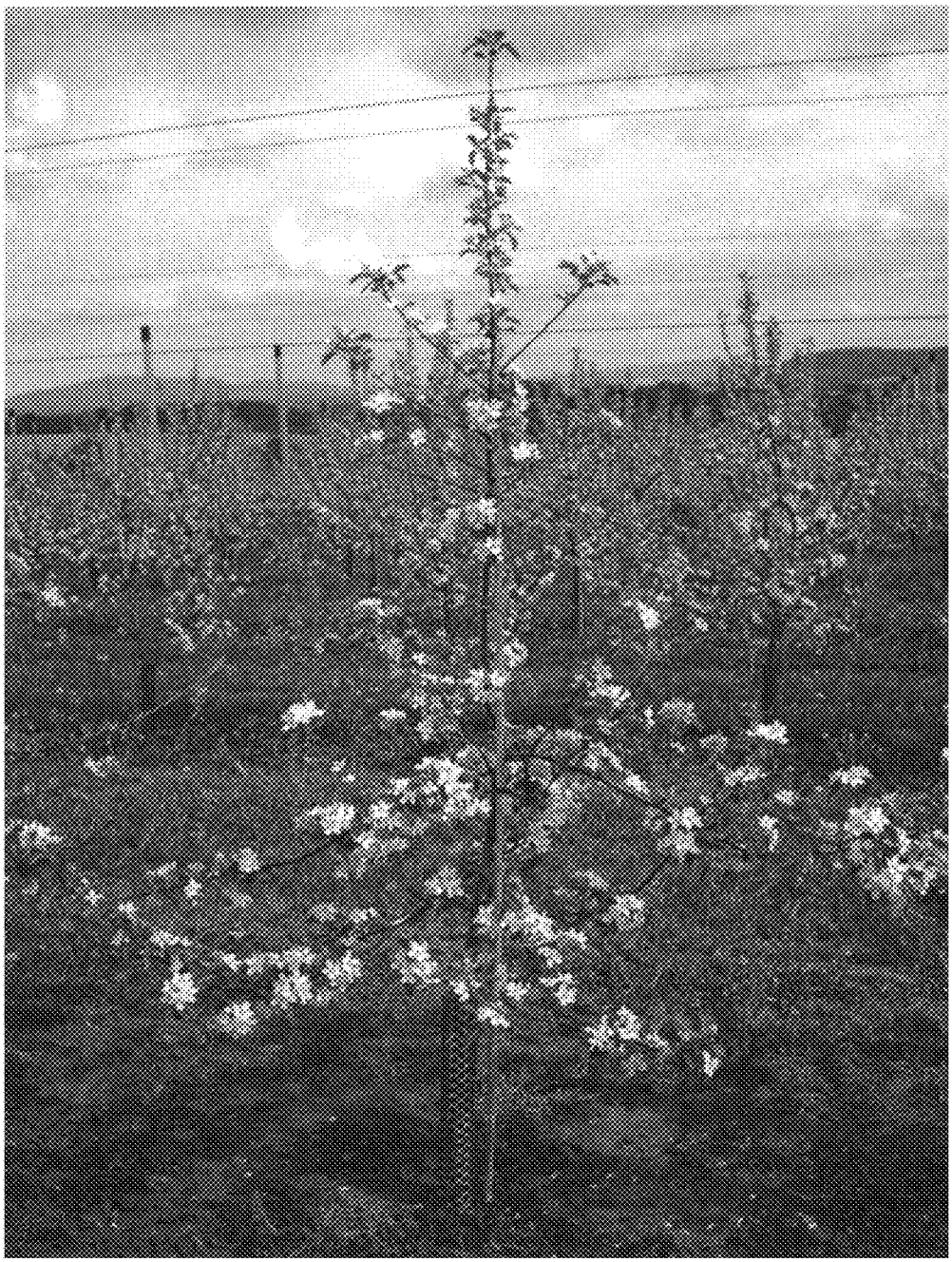
FIG. 6 illustrates a tree of the new variety showing canopy form at blossoming time at 6 years of age, grafted on M9 rootstock.
Figure 7:
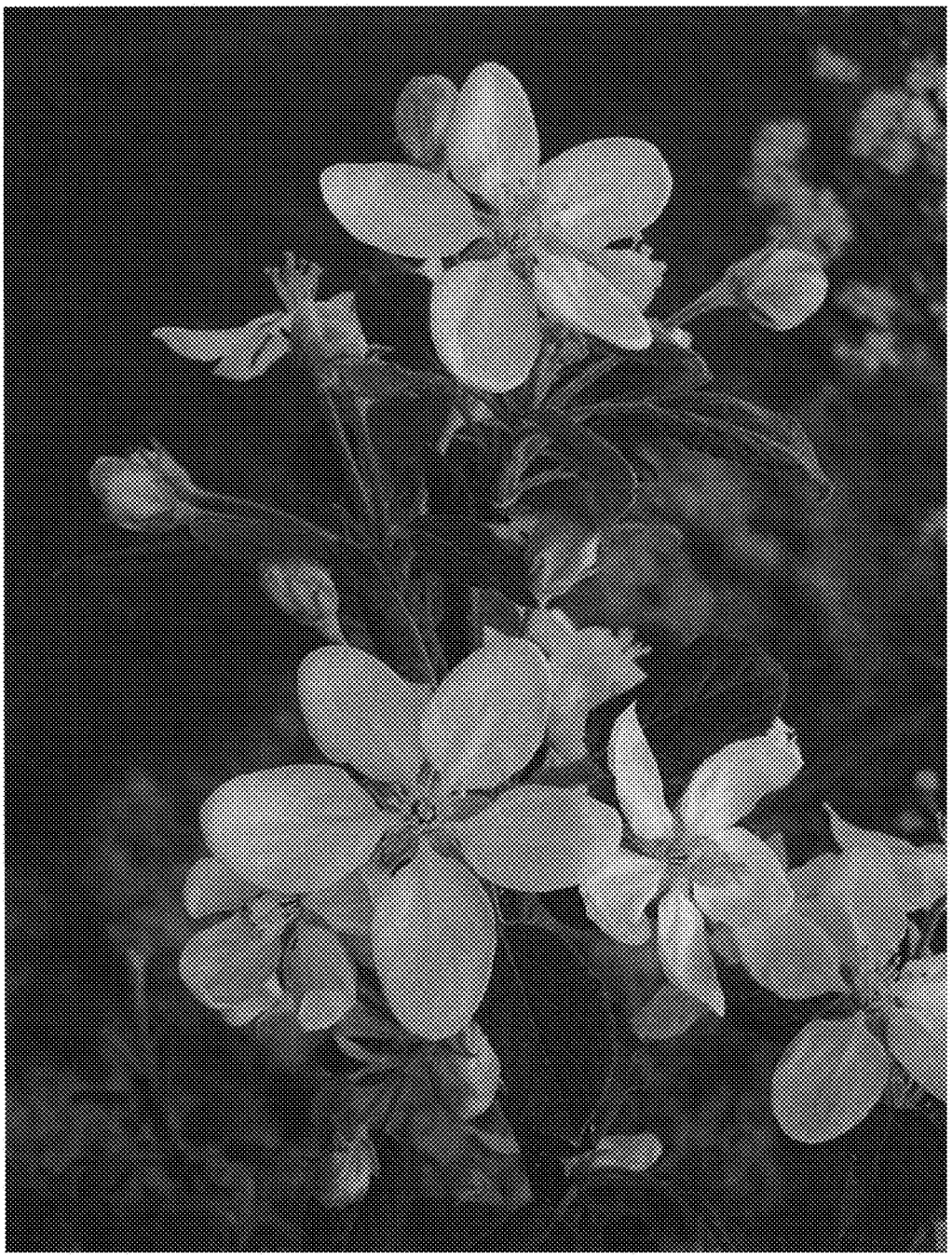
FIG. 7 illustrates details of blossoms of the new variety at the beginning of blossoming time from a six-year old tree.
Figure 8:
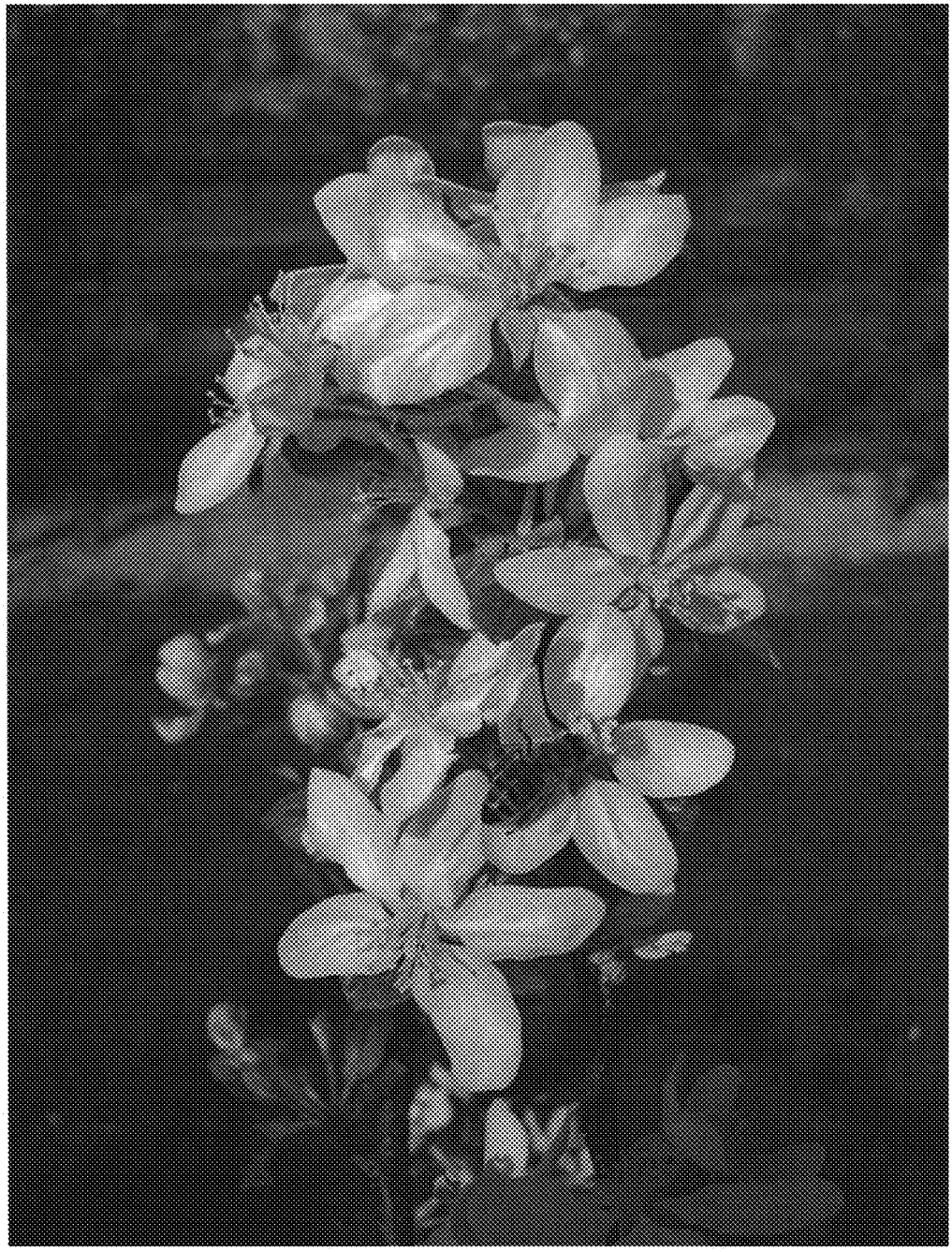
FIG. 8 illustrates details of blossoms of the new variety at full blossoming time from a six-year old tree.
Figure 9:
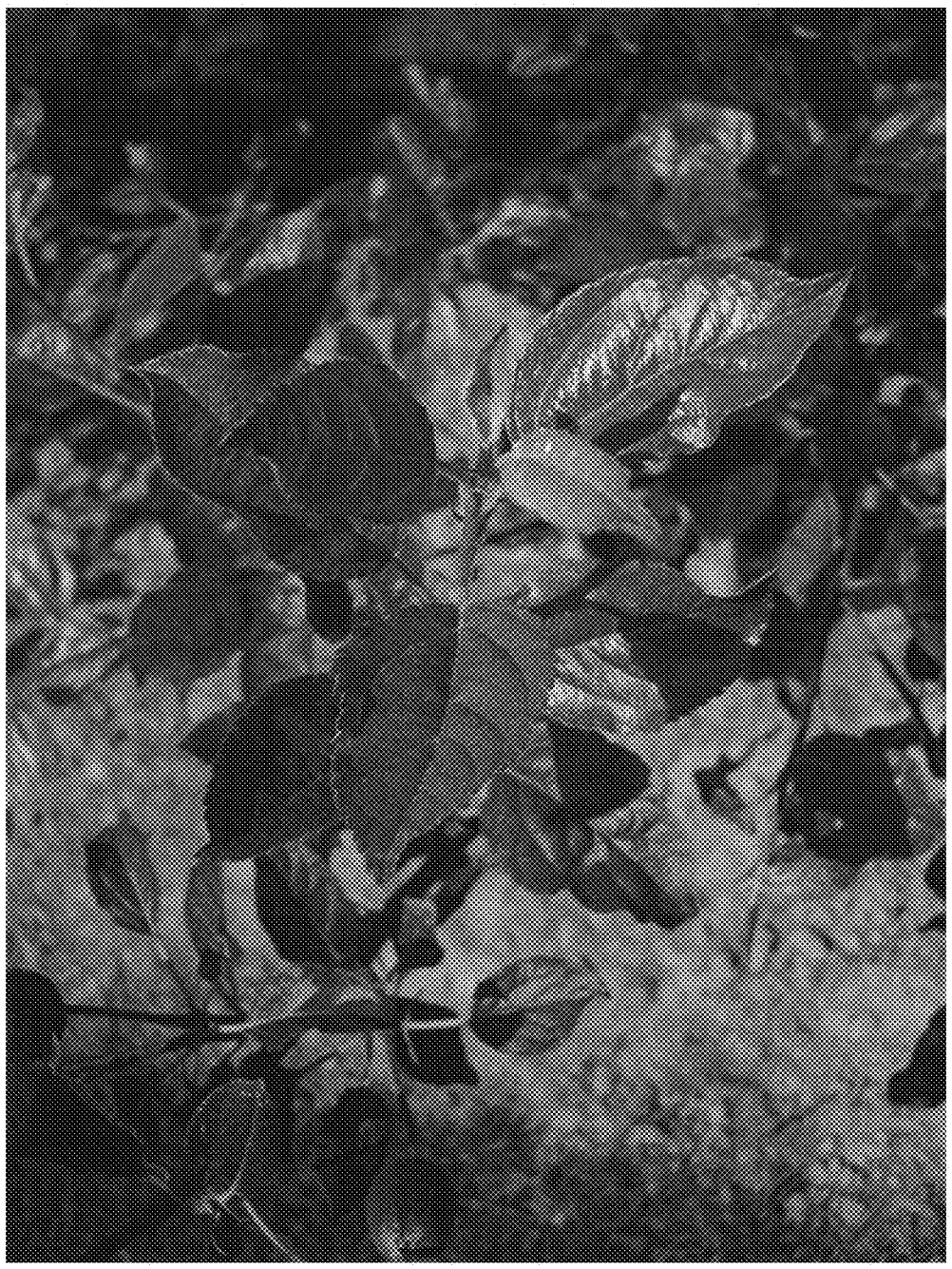
FIG. 9 illustrates a growing shoot of the new variety from a six-year old tree.
Figure 10:
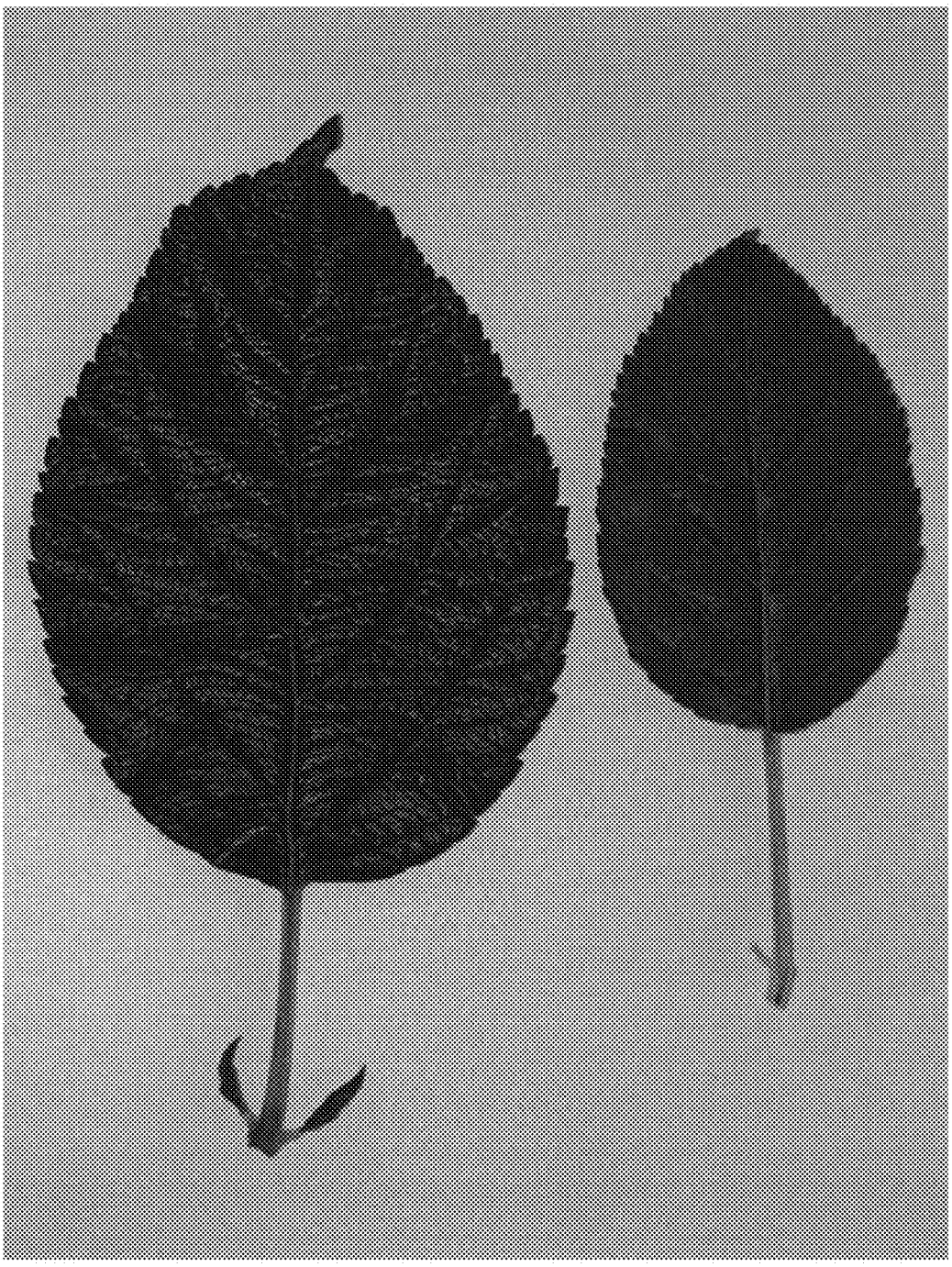
FIG. 10 illustrates a close-up view of a mature leaf and a young leaf of the new variety from a six-year old tree.

The following detailed description sets forth characteristics of the new cultivar. The new variety was grown under natural field conditions in The Czech Republic. The following fertilizer combination was used (Kg/ha/year): 55 parts nitrogen, 25 parts phosphorous, 60 parts potassium, 55 parts calcium, and 5 parts magnesium. Color references are primarily to The 1986 R.H.S. Colour Chart of The Royal Horticultural Society of London (in association with the Flower Council of Holland), Second Edition, and were identified under natural light.

TREE

Age: Approximately 4 years.
Size: Crown height of 3.0 m, width of 3.5 m.
Vigor: Moderate.
Density: Open.
Form: Spreading.
Production: Precocious.
Growth type: Ramified, with horizontal branching and a slightly weeping habit.
Bearing: Annual; on spurs and long shoots.
Average productivity: 13 kg per tree in third year after grafting on M9 rootstock.
Trunk:
- *Size*.—Approximately 9.0 cm in diameter at 30.0 cm from the soil line.
- *Surface texture*.—Smooth.
- *Bark color*.—Grey-Brown Group RHS 199A to 199B.
- *Lenticels*.—Length: 1.0 mm to 5.0 mm. Width: 0.5 mm to 1.0 mm. Color: Greyed-Yellow Group RHS 161C.
- *Density*.—Variable, with 6 to 8 lenticels on average per 1 $cm^2$.

Branches:
- *Overall description*.—Lacking a conventional branching system along the tree trunk.
- *Diameter*.—Main branches on the trunk are 2.5 cm. to 4.0 cm.
- *Surface texture*.—Smooth.
- *Color*.—Grey-Brown Group RHS 199B.
- *Form*.—Profuse branching.
- *Average crotch angle*.—About 80 to 90 degrees.
- *Bud arrangement*.—Alternate internode intervals from 2.5 cm to 3.0 cm.
- *Lenticels*.—Length: 1.0 mm to 4.0 mm. Width: 0.5 mm to 1.0 mm. Shape: Oval. Density: Variable, with 5 to 7 lenticels on average per 1 $cm^2$. Color: Greyed-Yellow Group RHS 161C.
- *Leaves*.—Length: Average of 75.0 mm. Width: Average of 53.0 mm. Form: Ovate. Texture: Smooth. Thickness: Medium. Base: Rounded and mostly symmetric. Apex: Abruptly. Margin: Crenate to bicrenate.
- *Pubescence*.—Upper surface: None present. Lower surface: Very fine.
- *Color*.—Young leaves: Upper surface: Yellow-Green Group RHS 144A. Lower surface: Yellow-Green Group RHS 147C. Mature leaves: Upper surface: Yellow-Green Group RHS 147A. Lower surface: Yellow-Green Group RHS 148B.
- *Petiole*.—Shape: Straight, with thickening at the base. Length: About 20.0 mm to 25.0 mm, averaging 22.5 mm. Diameter: About 1.0 mm to 1.5 mm in the middle. Color: Yellow-Green Group RHS 146C, with some Red Group RHS 53A near the base.
- *Stipule*.—Length: 0.8 cm. Shape: Elongated, with an acute apex. Color: Yellow-Green Group RHS 146A.
- *Veins*.—Description: Net-like, medium dense. Color: Upper surface: Yellow-Green Group RHS 144B to 144C. Lower surface: Yellow-Green Group RHS 145C to 144C.

Flower buds:
- *Pedicel*.—Length: 25.0 mm to 37.0 mm, averaging 30.0 mm. Diameter: 1.5 mm on average. Color: Predominantly Yellow-Green Group RHS 144A.
- *Bud*.—Length: 16.0 mm on average. Width: 12.0 mm on average. Color: Red-Purple Group RHS 62A, with White Group RHS 155C partly present.

Flowers:
- *Bloom timing*.—At the end of April to beginning of May (May $5^{th}$, on average) — at the same time as 'Golden Delicious'.
- *Pollination requirements*.—Self-sterile, needs pollinators such as such as *Malus* x *zumi* (crab apple) 'Golden Hornet' (unpatented).
- *Number of flowers per cluster*.—5 to 6.
- *Average flower diameter*.—About 50.1 mm (43.7 mm to 60.3 mm).
- *Fragrance*.—Faint.
- *Petals*.—Number: 5. Length: 22.0 mm to 25.0 mm, averaging 24.0 mm. Width: 15.0 mm to 17.0 mm, averaging 16.0 mm. Shape: Broadly ovate. Apex: Obtuse. Base: Rounded. Aspect: Positioned mostly touching. Margin: Entire. Texture and appearance: Soft and smooth. Color: When opening: Upper surface: Red-Purple Group RHS 62A, with White Group RHS 155C partly present. Lower surface:

Red-Purple Group RHS 62B, with White Group RHS 155C partly present. Fully opened: Upper surface: Red-Purple Group RHS 62A, with White Group RHS 155C partly present. Lower surface: Red-Purple Group RHS 62C to 62D, with White Group RHS 155C partly present.

*Sepals*.—Number: 5 (average). Shape: Long-conical; pointed; apex is acute; sepal bases linked together. Margin: Entire. Texture: Finely pubescent. Length: 11.0 mm to 16.0 mm from the union, averaging 13.0 mm. Width: 3.0 mm in the middle. Color: Upper surface: Yellow-Green Group RHS 144B, with a Red-Purple Group RHS 60A apex. Lower surface: Yellow-Green Group RHS 144C, with a Red-Purple Group RHS 60A apex.

*Stamens*.—Number (per flower): 20. Filament length: 8.0 mm to 13.0 mm.

*Anthers*.—Shape: Oval. Length: 2.0 mm. Color: Yellow Group RHS 10B.

*Pollen*.—Color: Yellow Group RHS 7C. Amount (generally): Medium.

*Pistils*.—Length: 18.0 mm on average.

*Style*.—Length: 14.0 mm on average. Color: Yellow-Green Group RHS 144B.

*Stigma*.—Shape: Curved at distal end, rounded at the top. Color: Yellow-Green Group RHS 144C.

Fruit:

*Maturity when described*.—Eating maturity after two months in common storage.

*Date of picking*.—October of 2017.

*Size*.—Axial diameter: Predominantly about 67.0 mm. Transverse diameter: Predominantly about 73.0 mm.

*Weight per fruit*.—Average of 149 g (from 126 g to 188 g).

*Form*.—Conical.

*Cavity*.—Description: Funnel-shaped, russeting is rare. Depth: Average of 14.0 mm. Breadth: Average of 32.0 mm.

*Basin*.—Description: Funnel-shaped. Depth: Average of 9.0 mm. Width: Average of 27.0 mm.

*Calyx*.—Persistent with erect lobes.

Skin:

*Thickness*.—Medium.

*Texture*.—Smooth, if no russeting occurs; medium, if russeting occurs.

*Tendency to crack*.—Absent.

*Color*.—Overcolor of Red Group RHS 46A to Greyed-Purple Group RHS 187B.

*Ground color*.—Yellow Group RHS 11A.

Flesh:

*Aroma*.—Medium and similar to tropical fruits.

*Color*.—Yellow Group RHS 11C.

*Texture*.—Finely grained and firm.

*Eating quality*.—Very good, with a very high sugar/acid ratio (about 40:1).

Core:

*Bundle area*.—Onion-shaped on longitudinal section, locules half-closed on cross section, having weakly distinct vascular strands.

*Calyx tube*.—9.0 mm.

*Depth of tube to shoulder*.—About 9.0 mm.

*Styles*.—Persistent as dry residues, closed with calyx lobes.

*Stamens*.—Persistent as dry residues, closed with calyx lobes.

*Seed cells*.—Wall: Cracked. Depth: 12.0 mm. Breadth: 8.0 mm on cross section. Longitudinal section: About 21.0 mm (length of seed cell).

Seeds:

*Number perfect*.—8.

*Number in one cell*.—1 to 2.

*Length*.—7.0 mm.

*Breadth*.—5.0 mm.

*Form*.—Long conical with an acute tip.

*Color*.—Greyed-Orange Group RHS 166A.

Stem:

*Length*.—21.0 mm to 36.0 mm, averaging 27.0 mm.

*Width*.—2.0 mm on average.

*Color*.—Yellow-Green Group RHS 152B at the base to Greyed-Purple Group RHS 187B at the top.

Use: As a late ripening, dessert apple variety that exhibits $V_f$-resistance against scab and produces fruits of very good eating quality with a very sweet taste.

Shipping quality: Very good.

Keeping quality: Very good—about five to six months in common storage.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab.

We claim:

1. A new and distinct variety of *Malus domestica* (Borkh.) apple tree plant substantially as is herein described and illustrated.

* * * * *